(12) United States Patent
Howell et al.

(10) Patent No.: US 9,271,921 B2
(45) Date of Patent: *Mar. 1, 2016

(54) COSMETIC COMPOSITIONS HAVING PERSISTENT TIGHTENING EFFECTS

(71) Applicant: Avon Products, Inc., Suffern, NY (US)

(72) Inventors: Ashley L. Howell, Oakland, NJ (US); Bing C. Mei, Mahwah, NJ (US)

(73) Assignee: Avon Products, Inc., New York, NY (US)

( * ) Notice: Subject to any disclaimer, the term of this patent is extended or adjusted under 35 U.S.C. 154(b) by 32 days.

This patent is subject to a terminal disclaimer.

(21) Appl. No.: 13/826,724

(22) Filed: Mar. 14, 2013

(65) Prior Publication Data

US 2013/0202546 A1  Aug. 8, 2013

Related U.S. Application Data (63) Continuation-in-part of application No. 13/325,670, filed on Dec. 14, 2011, now Pat. No. 8,771,656.

(51) Int. Cl.
| | |
|---|---|
| *A61K 8/81* | (2006.01) |
| *A61Q 19/08* | (2006.01) |
| *A61Q 5/06* | (2006.01) |
| *A61Q 1/02* | (2006.01) |
| *A61Q 1/04* | (2006.01) |
| *A61Q 1/10* | (2006.01) |
| *A61Q 1/12* | (2006.01) |

(52) U.S. Cl.
CPC ............... *A61K 8/8152* (2013.01); *A61Q 1/02* (2013.01); *A61Q 5/06* (2013.01); *A61Q 19/08* (2013.01); *A61Q 1/04* (2013.01); *A61Q 1/10* (2013.01); *A61Q 1/12* (2013.01)

(58) Field of Classification Search
CPC .... A61Q 19/08; A61K 8/8152; A61K 8/8135
USPC ............................................ 424/70.16, 78.03
See application file for complete search history.

(56) References Cited

U.S. PATENT DOCUMENTS

| | | | |
|---|---|---|---|
| 4,795,631 A * | 1/1989 | Sheehan | ......................... 424/64 |
| 4,976,961 A | 12/1990 | Norbury et al. | |
| 5,993,831 A | 11/1999 | Ribier et al. | |
| 6,228,354 B1 | 5/2001 | Jeng | |
| 6,296,858 B1 | 10/2001 | Agostini et al. | |
| 6,592,854 B1 | 7/2003 | Dupuis | |
| 7,053,034 B2 | 5/2006 | Shefer et al. | |
| 7,323,162 B2 | 1/2008 | Martin et al. | |
| 7,632,905 B2 | 12/2009 | Boupat et al. | |
| 8,771,656 B2 | 7/2014 | Howell et al. | |
| 2005/0186169 A1 | 8/2005 | Charbit | |
| 2006/0127427 A1 | 6/2006 | Vernice et al. | |
| 2008/0262122 A1 | 10/2008 | Ueno et al. | |
| 2009/0285866 A1 * | 11/2009 | Afriat et al. | ................... 424/401 |
| 2011/0268688 A1 | 11/2011 | McCarthy et al. | |
| 2012/0213725 A1 | 8/2012 | Galleguillos et al. | |
| 2012/0301416 A1 | 11/2012 | Marotta et al. | |

FOREIGN PATENT DOCUMENTS

| | | |
|---|---|---|
| EP | 0011806 B1 | 6/1980 |
| EP | 0705854 A1 | 4/1996 |
| FR | 2864895 A1 | 5/2001 |
| WO | 2005067870 A1 | 7/2005 |
| WO | 2008074675 A1 | 6/2008 |
| WO | 2008122993 A1 | 10/2008 |
| WO | 2009118763 A1 | 10/2009 |
| WO | 2012/156965 A1 | 11/2012 |

OTHER PUBLICATIONS

Author: Evonik, Title: EUDRAGIT L 100-55; downloaded from http://eudragit.evonik.com/product/eudragit/en/products-services/eudragit-products/enteric-formulations/I-100-55/pages/default.aspx, Oct. 31, 2014.*
Specification EUDRAGIT L 100 and EUDRAGIT S 500; Rohm GmbH & Co. K.G., Sep. 2004.
U.S. Appl. No. 14/284,757, filed May 22, 2014, Howell et al.

* cited by examiner

*Primary Examiner* — Johann R Richter
*Assistant Examiner* — Yanzhi Zhang
(74) *Attorney, Agent, or Firm* — David M. Joyal; Joan M. McGillycuddy (57) ABSTRACT

Cosmetic compositions are provided, which are capable of having a tightening and/or curling effect on a human integument when applied thereto. Cosmetic compositions according to the invention typically include a cosmetically acceptable vehicle and a pH-dependent film-forming polymer of either a poly(methacrylic acid-co-methyl methacrylate) or a poly(methacrylic acid-co-ethyl acrylate). The tightening and/or curling effect of these cosmetic compositions is prolonged and substantially resistant to environmental stresses such as increased heat or humidity.

25 Claims, 2 Drawing Sheets

COSMETIC COMPOSITIONS HAVING PERSISTENT TIGHTENING EFFECTS

CROSS-REFERENCE TO A PRIOR APPLICATION

This application claims the benefit of U.S. patent application Ser. No. 13/325,670, filed Dec. 14, 2011 entitled "Long-Lasting Easy Wash-off Cosmetic Compositions," incorporated herein by reference in its entirety for all purposes.

FIELD OF THE INVENTION

The present application generally relates to cosmetic compositions that provide prolonged tightening effects and/or curling effects on a human integument. More particularly, the application relates to cosmetic compositions having pH-dependent polymers capable of tightening and/or curling a human integument, in particular skin and/or eye lashes, for a prolonged period of time. The tightening effect and/or curling effect of these compounds are substantially resistant to environmental stresses such as heat and humidity.

BACKGROUND OF THE INVENTION

The main sign of aging skin in humans is the increased presence of fine lines, deep wrinkles, and sagging skin. These signs of aging are most noticeable on the hands and faces of individuals. Although active agents, such as α-hydroxy acids, β-hydroxy acids and retinoids, are known to combat the underlying causes of wrinkles and fine lines, the prolonged period of time over which administration of these agents is necessary for visible results is inconsistent with the consumer's desire for immediate relief from these signs of aging.

Various film forming agents have been used as tightening and/or tensioning agents. The tightening effect of the film forming agents results from tension on the underlying substrate generated by the film forming agent as it contracts during its drying process. Thus, when the film forming agents are applied to skin the tension is sufficient to draw the skin tight and thereby temporarily smooth fine lines, mitigate deep wrinkles, and lift sagging skin. These tightening agents also have beneficial effects on other human integuments such as eyelashes such that, when applied, the curl of the eyelash is enhanced lifting and improving the eyelash's appearance.

Historically, naturally occurring film forming agents such as albumin derived from egg white or bovine serum have been used. More recently synthetic polymers such as polyvinylpyrrolidone (PVP), polyimides, hydroxyethyl cellulose, polyvinyl alcohol, and acrylate/octylacrylamide copolymer have been used to obtain tightening effects and/or curling effects. However, the tightening and/or curling effects of these above-noted film forming agents are not particularly persistent and are often susceptible to environmental influences such as heat and humidity. For example, under conditions of high humidity compositions containing PVP are known to plasticize, thereby diminishing tension exerted upon the skin.

Accordingly, there is a continuing need in the art for cosmetic compositions that provide a prolonged tightening and/or curling effect substantially resistant to environmental factors such as heat and humidity.

Certain pH-dependent products are known in the art. For example, U.S. Pat. No. 5,993,831 to Ribier et al., incorporated herein by reference in its entirety, is directed to compositions containing nanoparticles of one or more pH-dependent polymers encapsulating an oily phase containing an active agent such as a cosmetic or pharmaceutical. The nanoparticles are said to be from 100 to 1000 nm in diameter, which allows the particles to slip between the outermost corneocytes of the stratum corneum without reaching the living epidermis.

As another example, U.S. Pat. No. 4,976,961 to Norbury et al., incorporated herein by reference in its entirety, is similarly directed to cosmetic emollient oils in microcapsules of pH-dependent polymers. Norbury's microcapsules are said to range in size from 50 to 2000 μm in diameter, and are typically curshed on the skin to release the oils contained therein. The microcapsule shell is said to include organic polymers such as phenolic aldehydes, urea-aldehydes, acrylic polymers, gelatin, and agar.

U.S. Pat. No. 7,053,034 to Shefer et al., incorporated herein by reference in its entirety, is directed to a controlled-release carrier system for targeted delivery of fragrances and active ingredients onto fabric, hair, and skin. Shefer's system is said to include solid hydrophobic nano-spheres encapsulated in a pH or salt sensitive micro-spheres. The micro-spheres are described as having an average sphere size in the range of from about 20 μm (micrometers) to about 100 μm, and the nano-spheres are said to have an average sphere size in the range of from about 0.01 μm to about 5 μm. Moreover, the micro-spheres may be made from such exemplary pH-sensitive materials as copolymers of acrylate polymers with amino substituents, acrylic acid esters, and polyacrylamides. The micro-spheres of Shefer are formed from high temperature melts emulsified into an aqueous phase.

U.S. Patent App. Pub. 2006/0127427 to Vernice et al., incorporated herein by reference in its entirety, describes a surface coated abrasive material, having a water-soluble abrasive core surrounded by a coating that is substantially insoluble in aqueous media during storage but becomes substantially water soluble upon application of substantially large quantities of water or adjustment of the pH of the aqueous medium.

Additionally, European Patents 11806 and 705854 disclose the use of pH-dependent polymers as pH responsive thickening agents.

SUMMARY OF THE INVENTION

It has surprisingly been found that certain film-forming, pH-dependent polymers may be employed within cosmetic compositions to provide tightening effects upon human integuments for a prolonged period of time. It has also been found that the tightening and/or curling effects of these compositions are substantially resistant to environmental factors such as heat and humidity.

In accordance with the foregoing objectives and others, the present invention provides a method for forming a cosmetic film on a human integument. The method includes applying to the human integument a cosmetic composition having a cosmetically acceptable vehicle, optionally, one or more colorants, and a pH-dependent film-forming polymer of poly (methacrylic acid-co-methyl methacrylate (e.g., Eudragit S100 and Eudragit L100); and/or poly(methacrylic acid-co-ethyl acrylate (e.g., Eudragit L100-55).

These and other aspects of the invention will be better understood by reading the following detailed description and appended claims.

In one embodiment, a method is utilized for improving the aesthetic appearance of skin effected by aging comprising topically applying thereto an effective amount of a pH-dependent film-forming polymer of poly(methacrylic acid-co-methyl methacrylate) with a ratio of methacrylic acid to methyl methacrylate of about 1:1 to about 1:2, an acid value of from about 150 to about 350 mg KOH/g, and a weight average molar mass between about 100,000 and about 150,000 g/mol, in a cosmetically acceptable vehicle for a time sufficient to achieve a tightening effect.

In another embodiment, the ratio of methacrylic acid to methyl methacrylate is about 1:1.

In another embodiment, the ratio of methacrylic acid to methyl methacrylate is about 1:2.

In another embodiment, the acid value is from about 150 to about 200 mg KOH/g.

In another embodiment, the acid value is from about 300 to about 350 mg KOH/g.

In another embodiment, the pH-dependent film forming polymer has a target pH of greater than about 6.

In another embodiment, the pH-dependent film forming polymer has a target pH of greater than about 7.

In another embodiment, a method for improving the aesthetic appearance of skin effected by aging comprising topically applying thereto an effective amount of a pH-dependent film-forming polymer of poly(methacrylic acid-co-ethyl acrylate) with a ratio of methacrylic acid to ethyl acrylate of about 1:1, an acid value of from about 300 to about 350 mg KOH/g, and a weight average molar mass between about 200,000 and about 350,000 g/mol, in a cosmetically acceptable vehicle for a time sufficient to achieve a tightening effect.

In another embodiment, the pH-dependent film forming polymer has a target pH of greater than about 5.5.

In another embodiment, the tightening effect is selected from the group consisting of:

reduction and/or mitigation of the appearance of fine lines and/or wrinkles;

improvement in skin tautness;

improvement in skin appearance negatively impacted by aging and or menopause; and reduction or mitigation of the appearance of sagging skin.

In another embodiment, the tightening effect is an improvement in skin tightness of at least about 10%.

In another embodiment, the tightening effect is an improvement in skin tightness of at least about 20%.

In another embodiment, the tightening effect is an improvement in skin tightness of at least about 25%.

In another embodiment, the pH-dependent film-forming polymer is present in an amount of about 0.001 wt % to about 90% of the total weight of the composition.

In another embodiment, the pH-dependent film forming polymer is present in an amount of about 0.01 wt % to about 50% of the total weight of the composition.

In another embodiment, the ph-dependent film forming polymer is present in an amount of about 0.1 wt % to about 30% of the total weight of the composition.

In another embodiment, the pH-dependent film forming polymer is in combination with a retinoid.

In another embodiment, the pH-dependent film forming polymer is not in the form of a microcapsule.

In another embodiment, a method for providing a curling effect to an eyelash in need thereof comprising applying to said eyelash a cosmetic composition having a cosmetically acceptable vehicle, optionally one or more colorants, and an effective amount of a pH-dependent film-forming polymer of poly(methacrylic acid-co-methyl methacrylate) with a ratio of methacrylic acid to methyl methacrylate of about 1:1 to about 1:2, an acid value of from about 150 to about 350 mg KOH/g, and a weight average molar mass between about 100,000 and about 150,000 g/mol.

In another embodiment, the ratio of methacrylic acid to methyl methacrylate is about 1:1.

In another embodiment, the ratio of methacrylic acid to methyl methacrylate is about 1:2.

In another embodiment, the acid value is from about 150 to about 200 mg KOH/g.

In another embodiment, the acid value is from about 300 to about 350 mg KOH/g.

In another embodiment, the pH-dependent film forming polymer has a target pH of greater than about 6.

In another embodiment, the pH-dependent film forming polymer has a target pH of greater than about 7.

In another embodiment, a method for providing a curling effect to an eyelash in need thereof comprising applying to said eyelash a cosmetic composition having a cosmetically acceptable vehicle, optionally one or more colorants, and an effective amount of a pH-dependent film-forming polymer of poly(methacrylic acid-co-ethyl acrylate) with a ratio of methacrylic acid to ethyl acrylate of about 1:1, an acid value of from about 300 to about 350 mg KOH/g, and a weight average molar mass between about 200,000 and about 350,000 g/mol.

In another embodiment, the pH-dependent film forming polymer has a target pH of greater than about 5.5.

In another embodiment, the cosmetic composition is a mascara.

In another embodiment, the pH-dependent film-forming polymer is present in an amount of about 0.001 wt % to about 90% of the total weight of the composition.

In another embodiment, the pH-dependent film forming polymer is present in an amount of about 0.01 wt % to about 20% of the total weight of the composition.

In another embodiment, the pH-dependent film forming polymer is present in an amount of about 0.1 wt % to about 10% of the total weight of the composition.

In another embodiment, the pH-dependent film forming polymer is not in the form of a microcapsule.

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, and some features may be exaggerated to show details of one embodiment's components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

The present invention provides for cosmetic compositions which comprise an effective amount of a pH dependent film forming polymer that provides a curling and/or tightening effect upon topical application to a human. The curling effect upon lashes may include an enhanced degree and or percentage of curling of the eyelashes. The tightening effect of such compositions may increase the tightness of the skin resulting in a smoothing out of the skin and immediately inducing, indeed bringing about, the disappearance and/or mitigation of the appearance of wrinkles, fine lines, and/or sagging skin. Tightening effects include without limitation: (1) reduction and/or mitigation of the appearance of fine lines and/or wrinkles; (2) improvement in skin tautness; (3) improvement in skin appearance negatively impacted by aging and or menopause; (4) reduction or mitigation of the appearance of sagging skin; and/or (5) improvement in the form of an increased feeling of skin tautness. In practice, the compositions of the invention are applied to a human integument (e.g., skin, lashes, lips, hair, etc.) which suffers from a deficiency or loss in any of the foregoing attributes or which would otherwise benefit from improvement in any of the foregoing attributes. Suprisingly, these effects may be maintained for prolonged periods of time under adverse environmental conditions when the current inventive cosmetic compositions are applied.

The cosmetic compositions may be in the form of solids (e.g., powders and pressed powders); suspensions; serums; lotions; aqueous, dilute alcoholic or oily gels; dispersions; emulsions (e.g., oil-in-water emulsions and water-in-oil emulsions); liquids, and the like. As used herein, the term liquid is intended to include very thin to very viscous materials including non-Newtonian liquids having high initial viscosities (e.g., up to about 2,000,000 cps at 25° C.), as well as gels and other materials capable of dispensation from a container onto a human integument. Preferred cosmetics include, without limitation, mascara, foundation, sunscreen, pressed powder, eyeshadow, aqueous lip products (e.g., lipstick and lipgloss), skin cream, skin gel, and the like.

In one embodiment the composition is intended for use as a non-therapeutic treatment. In another embodiment, the composition is an article intended to be rubbed, poured, sprinkled, or sprayed on, introduced into, or otherwise applied to the human body for cleansing, beautifying, promoting attractiveness, or altering the appearance, in accordance with the US FD&C Act, sec. 201(i).

The cosmetic compositions comprise one or more pH-dependent, film-forming polymers. Generally, these polymers comprise anionic copolymers with monomers comprised of acrylic acid/acrylic acid derivatives. In particular, the copolymers may consist of methacrylic acid and methyl methacrylate or ethyl acrylate copolymers in a random, block, or alternating configuration. The polymers are insoluble in water at a pH below a trigger pH due to non-ionized (i.e., protonated) carboxylic acid groups. However, as the pH of a solution is increased to the trigger pH, the polymers experience ionization of the carboxylic acid group, resulting in increased aqueous solubility and consequent dissolution of the polymer and removal from the integument.

Without wishing to be bound to any particular theory, the inventors believe that the pH-dependent, film forming polymers within the tightening/curling cosmetic composition of the current invention contribute to the long-lasting and substantial environmental resistance of the compounds. In particular, it is hypothesized that the film-forming pH dependent polymers utilized within the current invention do not dissolve but remain as stable films at the pH of water. Therefore, the polymers are able to maintain their tightening and curling effects in the presence of ambient humidity and/or sweat (in other words, maintain tightening/curling effects of a film forming polymer at skin physiological pH).

All terms used herein are intended to have their ordinary meaning in the art unless otherwise provided. All concentrations are in terms of percentage by weight of the specified component relative to the entire weight of the cosmetic composition. Unless otherwise defined, the phrase "substantially free" refers to an amount of a component that is sufficiently low such that the component contributes no significant properties to the bulk and, in any event, will be less than 0.5% by weight and in one embodiment less than 0.1% by weight.

As used herein, the term "consisting essentially of" is intended to limit the invention to the specified materials or steps and those materials or steps that do not materially affect the basic and novel characteristics of the claimed invention, as understood from a reading of this specification. All percentages are by weight based on the total weight of the composition, unless otherwise indicated.

By "cosmetically acceptable" it is meant that a particular component is generally regarded as safe and nontoxic at the levels employed.

The term "active amount" refers to the amount of film-forming pH dependent polymer, absent diluent, solvent, carrier, filler or any other ingredient. An "amount effective" or an "effective amount" to provide a particular tightening and/or curling benefit to a human integument, e.g. skin, hair, eyelashes, lips, etc., refers to the "active amount" of film-forming pH dependent polymer required to provide a clinically measurable improvement in the particular manifestation of skin aging when applied for a time sufficient to provide a measurable improvement in the particular manifestation of aged skin.

The phrase "individual in need thereof" refers to a human who could benefit from improved dermal/integument (e.g. skin, hair, eyelashes, lips, etc.) appearance or health, including males or females.

In certain embodiments of the invention, the pH-dependent film-forming polymer typically has a molar ratio of methacrylic acid to ethyl acrylate of about 1:1, an acid value of from about 150 to about 350 mg KOH/g, and a weight average molar mass between about 200,000 and about 350,000 g/mol. Typically the pH-dependent film forming polymer may have the following structure:

wherein m and n are integers so that the weight average molar mass is between about 200,000 and about 350,000 g/mol and so that the molar ratio of methacrylic acid to ethyl acrylate is about 1:1. Examples of these polymers are available as EUDRAGIT® L 100-55 from Evonik Degussa-Huls Corporation and are generally insoluble at pH values less than about 6.

In further embodiments of the invention, the pH-dependent film-forming polymer typically has a molar ratio of methacrylic acid to methyl methacrylate of about 1:1 to about 1:2, an acid value of from about 150 to about 350 mg KOH/g, and a weight average molar mass between about 100,000 and about 150,000 g/mol. These pH-dependent film forming polymers may have the following structure wherein m and n are integers so that the weight average molar mass is between about 100,000 and about 150,000 g/mol and so that the molar ratio of methacrylic acid to methyl methacrylate is about 1:1 to about 1:2. Examples of these polymers are available as EUDRAGIT® S 100 and EUDRAGIT® L 100 from Evonik Degussa-Huls Corporation, and they are generally insoluble at pH values less than about 7 (EUDRAGIT® S 100)/less than about 6 (EUDRAGIT® L 100)/less than about 5.5 (EUDRAGIT® L 100-55).

Exemplary pH-dependent polymers according to the invention will comprise methacrylic acid and methyl methacrylate or ethyl acrylate copolymers in a molar ratio from about 1:1 to about 1:2 (e.g., about 1:1, and about 1:2). The polymers typically comprise an acid value of about 150 to about 350 mg KOH/g, including exemplary ranges such as, but not limited to, about 150 to about 200 mg KOH/g and about 300 KOH/g to about 350 KOH/g. Acid values of about 190 mg KOH/g and about 315 mg KOH/g are particularly preferred. Moreover, in certain embodiments, the methacrylic co-methyl methacrylate pH-dependent polymers will typically have an average molar mass from about 100,000 to about 150,000 g/mol, and most typically about 125,000 g/mol. In other embodiments, the methacrylic co-ethyl acrylate pH-dependent polymers will typically have an average molar mass from about 200,000 to about 350,000 g/mol, in one embodiment about 250,000 g/mol.

In one embodiment, pH-dependent film-forming polymers are sold under the names EUDRAGIT® S 100, EUDRAGIT® L 100, and EUDRAGIT® L100-55 by Evonik Degussa-Huls Corporation. Films or coatings of such polymers are insoluble at pH values less than about 7 (EUDRAGIT® S 100), less than about 6 (EUDRAGIT® L 100), and less than about 5.5 (EUDRAGIT® L 100-55). Accordingly, these polymers may be included in cosmetic compositions either alone or in combination, such that the pH-dependent solubility of a film produced thereby may be selected to be from about 5.5 to about 7, including but not limited to about 5.5, 5.6, 5.7, 5.8, 5.9, 6.0, 6.1, 6.2, 6.3, 6.4, 6.5, 6.6, 6.7, 6.8, 6.9 and 7.0. Such selection will typically be based on the desired use of the cosmetic composition. However, it may be broadly stated that the pH-dependent, film-forming polymers will be selected such that the film is insoluble in water at the prevalent environmental conditions. Accordingly, the film-forming polymers may be chosen such that the cosmetic composition is soluble at a pH greater than about 5.0, greater than about 5.5, greater than about 6.0, greater than about 6.5, greater than about 7.0, or greater than about 7.5, depending on the intended use.

The amount of pH-dependent polymer(s) present in the tightening compositions will typically range from about 0.1 to about 10% by weight of the composition, but may be higher or lower depending on the desired properties. Typically, the cosmetic compositions will comprise the pH-dependent polymers in an amount of from about 0.1% to about 10% by weight, more typically from about 0.2 to about 8% by weight, and most typically from about 0.5 to about 5% by weight. It has been found that cosmetic compositions comprising such pH-dependent polymers are both easy to apply to and remove from the skin, yet remain in contact with the skin for long periods of time, i.e. do not rub-off. Cosmetic compositions comprising pH-dependent polymers may remain on the skin for greater than about 4, about 12, about 24, about 48, or even greater than about 72 hours.

The film-forming polymer is not in the form of an encapsulant, and is particularly not utilized such as those described in U.S. Pat. Nos. 7,053,034, 4,976,961, 5,993,831 and U.S. Patent App. Pub. No. 2006/0127427, each of which is described above and incorporated herein by reference in their entirety. As used herein, the term "microcapsule" refers to a structure having a polymeric membrane (i.e., shell) surrounding a core material (e.g., an active ingredient). The term "microcapsule" is intended to be generic, and is not limited to a particular size (i.e., nano, micro, etc.).

Another embodiment of the invention encompasses compositions comprising a cosmetically or dermatologically acceptable formulation which is suitable for contact with living animal tissue, including human tissue, with virtually no adverse physiological effect to the user. Compositions embraced by this invention can be provided in any cosmetically and/or dermatologically suitable form, in one embodiment as a lotion or cream, but also in an anhydrous or aqueous base, as well as in a sprayable liquid form. Other suitable cosmetic product forms for the compositions of this invention include, for example, an emulsion, a cream, a balm, a gloss, a lotion, a mask, a serum, a toner, an ointment, a mousse, a patch, a pomade, a solution, a spray, a wax-based stick, a gellant-based stick or a towelette. In addition, the compositions contemplated by this invention can include one or more compatible cosmetically acceptable adjuvants commonly used and known by the skilled practitioner, such as colorants, fragrances, emollients, humectants, preservatives, vitamins, chelators, thickeners, *perilla* oil or *perilla* seed oil (WO 01/66067 to a "Method of Treating a Skin Condition,") and the like, as well as other botanicals such as aloe, chamomile, and the like, and as further described below.

The compositions can include a cosmetically acceptable vehicle. Such vehicles may take the form of any known in the art suitable for application to skin and may include water (e.g., deionized water); vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, dimethicone, dimethicone cross-polymer, polysiloxanes and their derivatives, such as organomodified derivatives; hydrocarbon oils such as mineral oil, petrolatum, isoeicosane and polyisobutene; polyols such as propylene glycol, glycerin, butylene glycol, pentylene glycol and hexylene glycol; waxes such as beeswax and botanical waxes; or any combinations or mixtures of the foregoing.

The vehicle may comprise an aqueous phase, an oil phase, an alcohol, a silicone phase or mixtures thereof. The cosmetically acceptable vehicle may also comprise an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. The emulsion may include an emulsifier, such as a nonionic, anionic or amphoteric surfactant.

The oil phase of the emulsion in one embodiment has one or more organic compounds, including emollients; humectants (such as butylene glycol, propylene glycol, Methyl gluceth-20, and glycerin); other water-dispersible or water-soluble components including thickeners such as veegum or hydroxyalkyl cellulose; gelling agents, such as high MW polyacrylic acid, i.e. CARBOPOL 934; and mixtures thereof. The emulsion may have one or more emulsifiers capable of emulsifying the various components present in the composition.

The compounds suitable for use in the oil phase include without limitation, vegetable oils; esters such as octyl palmitate, isopropyl myristate and isopropyl palmitate; ethers such as dicapryl ether; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; natural or synthetic waxes; and the like. Suitable hydrophobic hydrocarbon oils may be saturated or unsaturated, have an aliphatic character and be straight or branched chained or contain alicyclic or aromatic rings. The oil-containing phase may be composed of a singular oil or mixtures of different oils.

Hydrocarbon oils including those having 6-20 carbon atoms may be utilized, and in one embodiment they may have 10-16 carbon atoms. Representative hydrocarbons include decane, dodecane, tetradecane, tridecane, and $C_{8-20}$ isoparaffins. Paraffinic hydrocarbons are available from Exxon under the ISOPARS trademark, and from the Permethyl Corporation. In addition, $C_{8-20}$ paraffinic hydrocarbons such as $O_{12}$ isoparaffin (isododecane) manufactured by the Permethyl Corporation having the tradename Permethyl 99A™ are also contemplated to be suitable. Various commercially available $C_{16}$ isoparaffins, such as isohexadecane (having the tradename Permethyl®) are also suitable. Examples of volatile hydrocarbons include polydecanes such as isododecane and isodecane, including for example, Permethyl-99A (Presperse Inc.) and the $C_7$-$C_8$ through $C_{12}$-$C_{15}$ isoparaffins such as the Isopar Series available from Exxon Chemicals. A representative hydrocarbon solvent is isododecane.

The oil phase may comprise one or more waxes, including for example, rice bran wax, carnauba wax, ouricurry wax, candelilla wax, montan waxes, sugar cane waxes, ozokerite, polyethylene waxes, Fischer-Tropsch waxes, beeswax, microcrystalline wax, silicone waxes, fluorinated waxes, and any combination thereof.

Non-limiting emulsifiers include emulsifying waxes, emulsifying polyhydric alcohols, polyether polyols, polyethers, mono- or di-ester of polyols, ethylene glycol mono-stearates, glycerin mono-stearates, glycerin di-stearates, silicone-containing emulsifiers, soya sterols, fatty alcohols such as cetyl alcohol, acrylates, fatty acids such as stearic acid, fatty acid salts, and mixtures thereof. Emulsifiers may include soya sterol, cetyl alcohol, stearic acid, emulsifying wax, acrylates, silicone containing emulsifiers and mixtures thereof. Other specific emulsifiers that can be used in the composition of the present invention include, but are not limited to, one or more of the following: $C_{10-30}$ alkyl acrylate crosspolymer; Dimethicone PEG-7 isostearate, acrylamide copolymer; mineral oil; sorbitan esters; polyglyceryl-3-diisostearate; sorbitan monostearate, sorbitan tristearate, sorbitan sesquioleate, sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; Steareth-2, Steareth-10, and Steareth-20, to name a few. Additional emulsifiers are provided in the INCI Ingredient Dictionary and Handbook $11^{th}$ Edition 2006, the disclosure of which is hereby incorporated by reference in its entirety.

These emulsifiers typically will be present in the composition in an amount from about 0.001% to about 10% by weight, in particular in an amount from about 0.01% to about 5% by weight, and in one embodiment, from about 0.1% to about 3% by weight.

The oil phase may comprise one or more volatile and/or non-volatile silicone oils. Volatile silicones include cyclic and linear volatile dimethylsiloxane silicones. In one embodiment, the volatile silicones may include cyclodimethicones, including tetramer ($D_4$), pentamer ($D_5$), and hexamer ($D_6$) cyclomethicones, or mixtures thereof. Particular mention may be made of the volatile cyclomethicone-hexamethyl cyclotrisiloxane, octamethyl-cyclotetrasiloxane, and decamethyl-cyclopentasiloxane. Suitable dimethicones are available from Dow Corning under the name Dow Corning 200® Fluid and have viscosities ranging from 0.65 to 600,000 centistokes or higher. Suitable non-polar, volatile liquid silicone oils are disclosed in U.S. Pat. No. 4,781,917. Additional volatile silicones materials are described in Todd et al., "Volatile Silicone Fluids for Cosmetics", Cosmetics and Toiletries, 91:27-32 (1976). Linear volatile silicones generally have a viscosity of less than about 5 centistokes at 25° C., whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.). Linear, volatile silicones include low molecular weight polydimethylsiloxane compounds such as hexamethyldisiloxane, octamethyltrisiloxane, decamethyltetrasiloxane, and dodecamethylpentasiloxane, to name a few.

Non-volatile silicone oils will typically comprise polyalkylsiloxanes, polyarylsiloxanes, polyalkylarylsiloxanes, or mixtures thereof. Polydimethylsiloxanes are non-volatile silicone oils. The non-volatile silicone oils will typically have a viscosity from about 10 to about 60,000 centistokes at 25° C., in one embodiment between about 10 and about 10,000 centistokes, and in one embodiment still between about 10 and about 500 centistokes; and a boiling point greater than 250° C. at atmospheric pressure. Non limiting examples include dimethyl polysiloxane (dimethicone), phenyl trimethicone, and diphenyldimethicone. The volatile and non-volatile silicone oils may optionally be substituted with various functional groups such as alkyl, aryl, amine groups, vinyl, hydroxyl, haloalkyl groups, alkylaryl groups, and acrylate groups, to name a few.

The water-in-silicone emulsion may be emulsified with a nonionic surfactant (emulsifier) such as, for example, polydiorganosiloxane-polyoxyalkylene block copolymers, including those described in U.S. Pat. No. 4,122,029. These emulsifiers generally comprise a polydiorganosiloxane backbone, typically polydimethylsiloxane, having side chains comprising -(EO)$_m$— and/or —(PO)$_n$— groups, where EO is ethyleneoxy and PO is 1,2-propyleneoxy, the side chains being typically capped or terminated with hydrogen or lower alkyl groups (e.g., C$_{1-6}$, typically C$_{1-3}$). Other suitable water-in-silicone emulsifiers are disclosed in U.S. Pat. No. 6,685, 952. Commercially available water-in-silicone emulsifiers include those available from Dow Corning under the trade designations 3225C and 5225C FORMULATION AID; SILICONE SF-1528 available from General Electric; ABIL EM 90 and EM 97, available from Goldschmidt Chemical Corporation (Hopewell, Va.); and the SILWET series of emulsifiers sold by OSI Specialties (Danbury, Conn.).

Examples of water-in-silicone emulsifiers include, but are not limited to, dimethicone PEG 10/15 crosspolymer, dimethicone copolyol, cetyl dimethicone copolyol, PEG-15 lauryl dimethicone crosspolymer, laurylmethicone crosspolymer, cyclomethicone and dimethicone copolyol, dimethicone copolyol (and) caprylic/capric triglycerides, polyglyceryl-4 isostearate (and) cetyl dimethicone copolyol (and) hexyl laurate, and dimethicone copolyol (and) cyclopentasiloxane. In one embodiment examples of water-in-silicone emulsifiers include, without limitation, PEG/PPG-18/18 dimethicone (trade name 5225C, Dow Corning), PEG/PPG-19/19 dimethicone (trade name BY25-337, Dow Corning), Cetyl PEG/PPG-10/1 dimethicone (trade name Abil EM-90, Goldschmidt Chemical Corporation), PEG-12 dimethicone (trade name SF 1288, General Electric), lauryl PEG/PPG-18/18 methicone (trade name 5200 FORMULATION AID, Dow Corning), PEG-12 dimethicone crosspolymer (trade name 9010 and 9011 silicone elastomer blend, Dow Corning), PEG-10 dimethicone crosspolymer (trade name KSG-20, Shin-Etsu), dimethicone PEG-10/15 crosspolymer (trade name KSG-210, Shin-Etsu), and dimethicone PEG-7 isostearate.

The water-in-silicone emulsifiers typically will be present in the composition in an amount from about 0.001% to about 10% by weight, in another embodiment in an amount from about 0.01% to about 5% by weight, and in a further embodiment in an amount below 1% by weight.

The aqueous phase of the emulsion may include one or more additional solvents, including lower alcohols, such as ethanol, isopropanol, and the like. The volatile solvent may also be a cosmetically acceptable ester such as butyl acetate or ethyl acetate; ketones such as acetone or ethyl methyl ketone; or the like.

The oil-containing phase will typically comprise from about 10% to about 99%, about 20% to about 85%, or from about 30% to about 70% by weight, based on the total weight of the emulsion, and the aqueous phase will typically comprise from about 1% to about 90%, about 5% to about 70%, or from about 20% to about 60% by weight of the total emulsion.

In addition to the pH-dependent film forming polymers, the inventive cosmetic compositions may comprise any number of additional ingredients, such as, but not limited to: active ingredients (e.g., cosmetic, dermatological, and/or pharmaceutical), alcohols, allergy inhibitors, amino acids, anti-acne agents (e.g., salicylic acid), anti-aging agents, antiseptics, antifungal agents, antiperspirants, analgesics, anti-hair loss agents, anti-wrinkle agents, antibacterial agents, anti-microbial agents, anti-oxidants, anti-inflammatory agents, burn healing agents, colorants (e.g., lakes, pigments, and the like), de-pigmentation agents, deodorants, dyes, emollient (e.g., glycerin, butylene glycol), excipients, fatty substances, fillers, film formers (e.g., dimethicone acrylate copolymer, ethylhexyl acrylate copolymer), fragrances, free radical scavengers, glycerin, glycerin monostearate, glycerin distearate, hair growth agents, hair conditioners, hair softeners, hair moisturizers, herbal extracts, humectants (e.g., hyaluronic acid, orotic acid, lipoprotein), insect repellants, medication, moisturizers, non-active carrier oils (e.g., triglycerides, silicone oils, mineral oils), oils, peptides, polypeptides, proteins, perfumes, pigments, preservatives, plasticizers, reflectants, sebum absorbers, skin lightening agents, sunscreens, surfactants, tanning agents, thickening agents (e.g., hydroxyethylcellulose, xanthan gum, carbomer), Vaseline, vasoconstrictors, vasodilators, vitamins (e.g., Vitamin A, Vitamin E), water, waxes, and/or combinations thereof.

In addition, the tightening agents used according to the invention can also be used in combination with other compounds known to a person skilled in the art as tightening agents which have properties different from those of the agents used according to the invention. Proteins or a protein hydrolysates including, for example, milk proteins, such as lactalbumin, plant proteins, such as the soya protein sold under the name of Eleseryl by the company LSN, oats derivatives such as those sold under the name "Reductine" by the company Silab, or nucleic acids, such as DNA. It is possible, as an alternative form, to combine the tightening agents according to the invention with tightening polymers including, but not limited to, polyvinylpyrrolidone (PVP), polyimides, hydroxyethyl cellulose, polyvinyl alcohol, acrylate/octylacrylamide copolymer or polymers disclosed in FR-A-2, 758,084.

The composition of the present invention may also include other cosmetic ingredients such as, but not limited to, humectants, emollients, optical diffusers, moisturizers, anti-wrinkle ingredients, concealers, matte finishing agents, pigments, colorants, proteins, anti-oxidants, bronzers, chelating agents, emulsifiers, ultraviolet (UV) absorbing agents, oil absorbing agents, anti-foam agents, anti-tack agents, thickeners, fragrances, preservatives, anti-microbials, fungistats, neutralizing agents, vitamins, plasticizers, cohesion agents, basifying and acidifying agents, fillers, solvents, and mixtures thereof.

The compositions may contain additional ingredients such as alkalinizing agents, emulsifying agents, emollients, plasticizers, preservatives, humectants, moisturizing agents, solvents, and tonicity agents or active ingredients suitable to provide anti-aging benefits. Examples of preferred additional ingredients include glycerin.

Additional ingredients may optionally be added to the inventive compositions as detailed below.

Colorants or pigments: The compositions may comprise one or more cosmetic powders, for example, calcium aluminum borosilicate, PMMA, polyethylene, polystyrene, methyl methacrylate crosspolymer, nylon-12, ethylene/acrylic acid copolymer, boron nitride, Teflon, silica, or the like. Typically the compositions will include colorants or pigments to impart a desired color or effect. Examples are inorganic pigments, organic pigments, and/or lakes. Exemplary inorganic pigments include, but are not limited to, metal oxides and metal hydroxides such as magnesium oxide, magnesium hydroxide, calcium oxide, calcium hydroxides, aluminum oxide, aluminum hydroxide, iron oxides ($\alpha$-Fe$_2$O$_3$, $\gamma$-Fe$_2$O$_3$, Fe$_3$O$_4$, FeO), red iron oxide, yellow iron oxide, black iron oxide, iron hydroxides, titanium dioxide, titanium lower oxides, zirconium oxides, chromium oxides, chromium hydroxides, manganese oxides, cobalt oxides, cerium oxides, nickel oxides and zinc oxides and composite oxides and composite hydroxides such as iron titanate, cobalt titanate and cobalt aluminate. Non-metal oxides also contemplated to be suitable are alumina and silica, ultramarine blue (i.e., sodium aluminum silicate containing sulfur), Prussian blue, manganese violet, bismuth oxychloride, talc, mica, sericite, magnesium carbonate, calcium carbonate, magnesium silicate, aluminum magnesium silicate, silica, titanated mica, iron oxide titanated mica, bismuth oxychloride, and the like. Organic pigments can include, but are not limited to, at least one of carbon black, carmine, phthalocyanine blue and green pigment, diarylide yellow and orange pigments, and azo-type red and yellow pigments such as toluidine red, litho red, naphthol red and brown pigments, and combinations thereof.

Lakes generally refer to a colorant prepared from a water-soluble organic dye, (e.g., D&C or FD&C) which has been precipitated onto an insoluble reactive or adsorptive substratum or diluent. The term "D&C" as used herein means drug and cosmetic colorants that are approved for use in drugs and cosmetics by the FDA. The term "FD&C" as used herein means food, drug, and cosmetic colorants which are approved for use in foods, drugs, and cosmetics by the FDA. Certified D&C and FD&C colorants are listed in 21 C.F.R.§74.101 et seq. and include the FD&C colors Blue 1, Blue 2, Green 3, Orange B, Citrus Red 2, Red 3, Red 4, Red 40, Yellow 5, Yellow 6, Blue 1, Blue 2, Orange B, Citrus Red 2, and the D&C colors Blue 4, Blue 9, Green 5, Green 6, Green 8, Orange 4, Orange 5, Orange 10, Orange 11, Red 6, Red 7, Red 17, Red 21, Red 22, Red 27, Red 28, Red 30, Red 31, Red 33, Red 34, Red 36, Red 39, Violet 2, Yellow 7, Yellow 8, Yellow 10, Yellow 11, Blue 4, Blue 6, Green 5, Green 6, Green 8, Orange 4, Orange 5, Orange 10, Orange 11, and so on. Substrates suitable for forming lakes include, without limitation, mica, bismuth oxychloride, sericite, alumina, aluminum, copper, bronze, silver, calcium, zirconium, barium, and strontium, titanated mica, fumed silica, spherical silica, polymethylmethacrylate (PMMA), micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, nylon, silica silylate, silk powder, sericite, soy flour, tin oxide, titanium hydroxide, trimagnesium phosphate, walnut shell powder, and mixtures thereof. Suitable lakes include, without limitation, those of red dyes from the monoazo, disazo, fluoran, xanthene, or indigoid families, such as Red 4, 6, 7, 17, 21, 22, 27, 28, 30, 31, 33, 34, 36, and Red 40; lakes of yellow pyrazole, monoazo, fluoran, xanthene, quinoline, dyes or salt thereof, such as Yellow 5, 6, 7, 8, 10, and 11; lakes of violet dyes including those from the anthroquinone family, such as Violet 2. as well as lakes of orange dyes, including Orange 4, 5, 10, 11, and the like. Suitable lakes of D&C and FD&C dyes are defined in 21 C.F.R. §82.51.

The coloring agents may be optionally surface treated to for example make the particles more hydrophobic or more dispersible in a vehicle. The surface of the particles may, for example, be covalently or ionically bound to an organic molecule or silicon-based molecule or may be adsorbed thereto, or the particle may be physically coated with a layer of material. The surface treatment compound may be attached to the particle through any suitable coupling agent, linker group, or functional group (e.g., silane, ester, ether, etc). The compound may comprise a hydrophobic portion which may be selected from, for example, alkyl, aryl, allyl, vinyl, alkyl-aryl, aryl-alkyl, organosilicone, di-organosilicone, dimethicones, methicones, polyurethanes, silicone-polyurethanes, and fluoro- or perfluoro-derivatives thereof. Other hydrophobic modifiers include lauroyl lysine, Isopropyl Titanium Triisostearate (ITT), ITT and Dimethicone (ITT/Dimethicone) cross-polymers, ITT and Amino Acid, ITT/Triethoxycaprylylsilane Crosspolymer, waxes (e.g., carnauba), fatty acids (e.g., stearates), HDI/Trimethylol Hexylactone Crosspolymer, PEG-8 Methyl. Ether Triethoxysilane, aloe, jojoba ester, lecithin, perfluoroalcohol phosphate, and Magnesium Myristate (MM), to name a few.

An optional pigment component includes and alkyl silane surface-treated colorant consisting essentially of or comprising an alumina substrate (e.g., platelet shaped) and a pigment, dye, or lake bonded to the alumina substrate by an alkyl silane surface treatment. Typically, the alkyl silane will be octylsilane, and may be formed by treatment with triethoxy caprylylsilane. Non-limiting examples of such colorants include, but are not limited to, Alumina/Titanium Dioxide/Triethoxycaprylylsilane 1% (COVALUMINE™ Atlas White AS), Alumina/D&C Red Aluminum Lake CTD/Triethoxycaprylylsilane 1% (COVALUMINE™ Red Rose AS), Alumina/D&C Red Aluminum Lake CTD/Triethoxycaprylylsilane 1% (COVALUMINE™ Sonoma Red AS), Alumina/Black Iron Oxide CTD/Triethoxycaprylylsilane 1% (COVALUMINE™ Sonoma Black AS), Alumina/D&C Red #6 Aluminum Lake CTD/Triethoxycaprylylsilane 1% (COVALUMINE™ Fire Red AS), Alumina/Yellow Iron Oxide CTD/Triethoxycaprylylsilane 1% (COVALUMINE™ Sonoma Yellow AS), Alumina/D&C Blue #1 Aluminum Lake CTD/Triethoxycaprylylsilane 1% (COVALUMINE™ Astral Blue AS), Alumina/Carmine CTD/Triethoxycaprylylsilane 1% (COVALUMINE™ Campari AS), Alumina/Yellow #5 CTD/Triethoxycaprylylsilane 1% (COVALUMINE™ Sunburst AS), Alumina/Triethoxycaprylylsilane 1%, and combinations thereof, each of which is available from SENSIENT™ Cosmetic Technologies LCW.

Interference or pearl pigments may also be included. These are typically comprised of micas layered with about 50 to 300 nm films of $TiO_2$, $Fe_2O_3$, or $Cr_2O_3$ or the like. These include white nacreous materials, such as mica covered with titanium oxide or covered with bismuth oxychloride; and colored nacreous materials, such as titanium mica with iron oxides, titanium mica with ferric blue or chromium oxide, titanium mica with an organic pigment of the aforementioned type. If these materials are used, it is preferred that these materials are used collectively in an amount of less than 1.0 wt %. In one embodiment, the pearlescent component has a bismuth oxychloride based pearlescent ingredient or reflectance pearls. Bismuth oxychloride, better mimics the skin's natural reflectance, matches the skin's natural pearlescence more so than compounds such as titanium oxide. However, other pearlescent ingredients may be used. A preferred pearlescent component is called CHROMA-LITE, a combination of colored pigment bonded to BI-LITE 20 (bismuth oxychloride and mica) using calcium stearate. The CHROMA-LITE component is available in various shades/colors from Englehard Corporation (Iselin, N.J.). Other pearlescents include: MicaMira (Sandream Enterprises); SynMira (Sandream Enterprises); GlassMira (Sandream Enterprises); Xirona (EMD Performance Chemicals); Timiron (EMD Performance Chemicals); Colorna (EMD Performance Chemicals); Ronastar (EMD Performance Chemicals); RonaFlair (EMD Performance Chemicals); Reflecks (BASF); Duocrome (BASF); Chione (BASF).

The composition may comprise additional active ingredients having anti-aging benefits, as it is contemplated that synergistic improvements may be obtained with such combinations. Exemplary anti-aging components include, without limitation, botanicals (e.g., *Butea frondosa* extract); thiodipropionic acid (TDPA) and esters thereof; retinoids (e.g., all-trans retinoic acid, 9-cis retinoic acid, phytanic acid and others); hydroxy acids (including alpha-hydroxyacids and beta-hydroxyacids), salicylic acid and salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); barrier function enhancing agents (e.g., ceramides, glycerides, cholesterol and its esters, alpha-hydroxy and omega-hydroxy fatty acids and esters thereof, etc.); collagenase inhibitors; and elastase inhibitors; to name a few.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

In another embodiment, the topical compositions of the present invention may also include one or more of the following: a skin penetration enhancer, an emollient, a skin plumper, an optical diffuser, a sunscreen, an exfoliating agent, and an antioxidant.

An emollient provides the functional benefits of enhancing skin smoothness and reducing the appearance of fine lines and coarse wrinkles. Examples include isopropyl myristate, petrolatum, isopropyl lanolate, silicones (e.g., methicone, dimethicone), oils, mineral oils, fatty acid esters, cetyl ethylhexanoate, C12-15 alkyl benzoate, isopropyl isostearate, diisopropyl dimer dillinoeate, or any mixtures thereof. The emollient may be present from about 0.1 wt % to about 50 wt % of the total weight of the composition.

A skin plumper serves as a collagen enhancer to the skin. An example of a suitable skin plumper is palmitoyl oligopeptide. Other skin plumpers are collagen and/or other glycosaminoglycan (GAG) enhancing agents. When present, the skin plumper may comprise from about 0.1 wt % to about 20 wt % of the total weight of the composition.

An optical diffuser is a particle that changes the surface optometrics of skin, resulting in a visual blurring and softening of, for example, lines and wrinkles. Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, titania fibers, polyamide-6 powders or any mixtures thereof. When present, the optical diffuser may be present from about 0.01 wt % to about 20 wt % of the total weight of the composition.

A sunscreen for protecting the skin from damaging ultraviolet rays may also be included. In one embodiment sunscreens may include those with a broad range of UVB and UVA protection, such as octocrylene, avobenzone (Parsol 1789), octyl methoxycinnamate, octyl salicylate, oxybenzone, homosylate, benzophenone, camphor derivatives, zinc oxide, and titanium dioxide. When present, the sunscreen may comprise from about 0.01 wt % to about 70 wt % of the composition.

Suitable exfoliating agents include, for example, alphahydroxyacids, beta-hydroxyacids, oxaacids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. In one embodiment an exfoliating agent is glycolic acid. When present, the exfoliating agent may comprise from about 0.1 wt % to about 80 wt % of the composition.

Antioxidants scavenge free radicals from skin, protecting the skin from environmental aggressors. Examples of antioxidants that may be used in the present compositions include compounds having phenolic hydroxy functions, such as ascorbic acid and its derivatives/esters; alpha-hydroxyacids; beta-carotene; catechins; curcumin; ferulic acid derivatives (e.g. ethyl ferulate, sodium ferulate); gallic acid derivatives (e.g., propyl gallate); lycopene; reductic acid; rosmarinic acid; tannic acid; tetrahydrocurcumin; tocopherol and its derivatives (e.g., tocopheryl acetate); uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may comprise an antioxidant in one embodiment from about 0.001 wt % to about 10 wt %, and in one embodiment from about 0.01 wt % to about 5 wt %, of the total weight of the composition.

Other conventional additives include: vitamins, such as tocopherol and ascorbic acid; vitamin derivatives such as ascorbyl monopalmitate; thickeners such as hydroxyalkyl cellulose; gelling agents; structuring agents such as bentonite, smectite, magnesium aluminum silicate and lithium magnesium silicate; metal chelating agents such as EDTA; pigments such as zinc oxide and titanium dioxide; colorants; emollients; and humectants.

Fillers: Fillers can also optionally be added, in an amount from about 1 to about 20%, in one embodiment from about 1% to about 10% by weight of the final composition. Examples of fillers include, but are not limited to, silica, PMMA, nylon, alumina, barium sulfate, or any other filler typically used in such compositions.

Film formers: Polymeric film formers include cellulosics, polyolefins, polyvinyls, polacrylates, polyurethanes, silicones, silicone acrylates, polyamides, polyesters, fluoropolymers, polyethers, polyacetates, polycarbonates, polyimides, rubbers, epoxies, formaldehyde resins, and homopolymers and copolymers of any of the foregoing.

Waxes: Waxes which may be used in the invention include, but are not limited to, linear polyethylene, microcrystalline petroleum wax, carnauba wax, lignite wax, ouricouri wax, rice bran wax, castor wax, mortar wax, stearone, acrawax, bayberry wax, castor wax, Japan wax, ozokerite, beeswax, candelilla wax, petrolatum, ceresin wax, cocoa butter, illipe butter, esparto wax, shellac wax, ethylene glycol diesters or triesters of $C_{18}$-$C_{36}$ fatty acids, cetyl palmitate, paraffin wax, hard tallow, lanolin, lanolin alcohol, cetyl alcohol, glyceryl monostearate, sugarcane wax, jojoba wax, stearyl alcohol, silicone waxes, and combinations thereof.

It is understood to those skilled in the art that any other cosmetically acceptable ingredients, i.e., those included in the CFTA Cosmetic Ingredient Dictionary, 3rd Ed., may be used.

The above-described topical compositions are particularly useful as skin-tightening products for improving the appearance of skin. Such topical compositions can be applied to skin around the eyes, chin, neck and other facial areas to reduce sagginess of the skin and appearance of any wrinkle or fine line there-around, and it can also be applied to other bodily areas containing saggy or wrinkled skin. The resulting polymeric film provides immediate, visible skin-tightening and wrinkle-reduction effects. The film is effective in reducing both fine lines and deeper, greatly visible wrinkles. The tightening effect of such compositions provides the benefits of a: (1) reduction and/or mitigation of the appearance of fine lines and/or wrinkles; (2) improvement in skin tautness; (3) improvement in skin appearance negatively impacted by aging and or menopause; and/or (4) reduction or mitigation of the appearance of sagging skin. Further, the polymer film is biocompatible and comfortable to wear, and can therefore be left on the skin for a relatively long period of time to provide long-term skin benefits.

Figure 1:
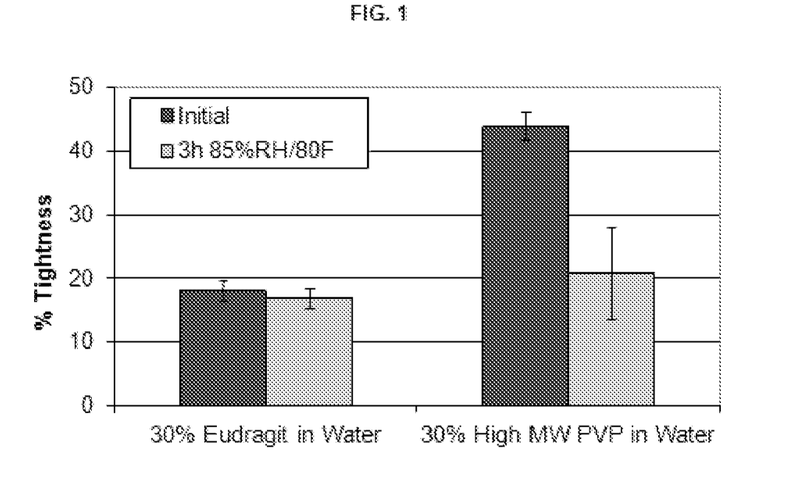
FIG. 1 is a bar chart illustrating the increase in skin tightness observed in synthetic Bioskin substrates after application of a cosmetic composition formulated according to one embodiment of the present invention in comparison with those observed after application of a composition containing PVP. Results shown reflect skin tightness reading obtained at: (1) initial administration and (2) three hours of increased temperatures (@ 80° F.) and humidity (85% relative humidity (RH)).
Figure 2:
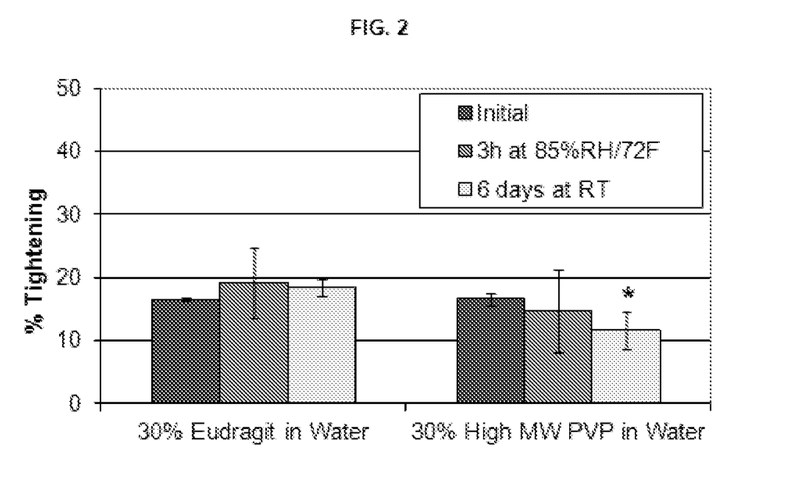
FIG. 2 is a bar chart illustrating the increase in skin tightness observed in synthetic BioSkin substrates after application of a cosmetic composition formulated according to one embodiment of the present invention in comparison with those observed after application of a composition containing PVP. Results shown reflect skin tightness readings obtained at: (1) initial administration, (2) three hours of increased temperatures (72° F.) and humidity (85% RH), and (3) six days after application.

Further, as noted below in Example 1, and FIGS. 1 and 2, the tightening effect of the cosmetic compositions of the current invention is persistent. FIG. 1 shows that a neat cosmetic composition of a film-forming pH dependent polymer of the current cosmetic composition (30% EUDRAGIT L100-55 in water) maintained the same level of tightening effect after exposure to three hours of high temperatures (@80° C.) and high humidity (85% RH) as when it was first applied. The neat composition of PVP (30% high MW PVP in water) lost half of its initial tightening effect over the same period. See FIG. 1. For both the HMV PVP and the Eudragit, the bars on the graph represent (left to right) measurements at initial and 3 hour timepoints. Further, as shown within FIG. 2, the neat cosmetic composition of a film-forming pH dependent polymer of the current cosmetic composition (30% EUDRAGIT L100-55 in water) maintained the same level of tightening six days after its application as when it was first applied onto a synthetic skin substrate. Whereas, the PVP neat composition (30% PVP in water) showed a statistically significant drop in its tightening effect over the same period. For both the HMV PVP and the Eudragit, the bars on the graph represent (left to right) measurements at initial, 3 hour and 6 day timepoints.

The methods of application in the present invention will depend on the ultimate intended use of composition. The topical composition can be applied locally to the saggy or wrinkled skin, or it can be applied to the entire body of the user. The topical composition of the present invention may be applied to the skin on an as-needed basis, to achieve immediate wrinkle reduction results (typically observable within five or ten minutes). Alternatively, the topical composition can be applied to the skin repeatedly according to a pre-set schedule. The topical composition of the present invention may be applied directly to clean skin, before application of any moisturizer, foundation, make-up, etc. Alternatively, the topical composition of the present invention can be applied over moisturizer, and optionally over foundation and/or make-up. The amount of the topical composition applied each time, the area of application, the duration of application, and the frequency of application can vary widely, depending on the specific need of the user. For example, the topical composition can be applied for a period of at least one month and at a frequency ranging from about once per week, to about twice a week, to about every other day, to about once per day, to about two times per day. For another example, the topical composition is applied for a period of about six months and at a frequency ranging from about three times a week to about three times per day, and in one embodiment about once or twice per day. The topical composition may comprise the active components at a total amount ranging from about 0.001% to about 90%, in one embodiment from about 0.01% to about 50%, and more in one embodiment from about 0.1% to about 30%. However, it should be noted that it is well within the purview of the skilled artisan, such as a dermatologist or other health care provider, to tailor the dosages of the topical compositions of the present invention according to specific patient needs.

The effect of a composition on skin tightness or the appearance of lines, wrinkles, or saggy skin may be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin), and/or evaluating tightness using procedure noted below in Example 1. In one embodiment, the compositions of the current invention demonstrate an improvement in skin tightness of at least about 1%, in another embodiment at least about 5%, in another embodiment at least about 7.5%, in another embodiment at least about 10%, in another embodiment at least about 20%, in a further embodiment about 25% and in yet another embodiment about 27.5%.

In a further embodiment, a mascara composition is provided for in accordance with this invention. The mascara may be applied to the eyelashes as often as needed or desired to impart the desired curling effect. The composition is typically applied to the lower side of the natural hairs with an outward, extending motion (in the general direction of the extension of the hairs). Application results in a film coating on at least a portion of the eyelashes. The composition then dries through evaporation of solvent and any other volatiles. Periodic re-application may be necessary in the normal course as the film coating wears off. Typically, the composition will be applied once per day. If desired the composition may be applied twice or more per day. The composition will provide curl retention and longevity for in one embodiment about 8 or more hours per day, more in one embodiment about 10 or more hours per day, and most in one embodiment about 12 or more hours per day. Longevity means exhibiting substantially no flaking or brittleness on the lash and exhibiting substantially no smudging or smearing.

The cosmetic composition for curling effect may comprise the pH dependent film forming polymers active components at a total amount ranging from about 0.001% to about 90%, in one embodiment from about 0.01% to about 20%, and more in one embodiment from about 0.1% to about 10%.

In the present method, application of the mascara composition provides a degree of curl to eyelashes corresponding a curl of 7.5% or more, in one embodiment about 10% or more, and more in one embodiment about 15% or more by the film former shrinkage test noted below. Degree of curl is determined by measuring degree of curl observed in artificial eyelashes after application of the mascara composition. Bundles of artificial lashes are glued to the periphery of a holding cylinder. The mascara composition is applied to the lashes for fourteen strokes with a mascara brush. After at least ten minutes of drying time, an image, such as photographic or digital image, is taken from a side view. Percent (%)Curl=$[(R-L)/R] \times 100\%$. Length measurement (L) is determined by measuring from the root of a bundle and the tip of a lash in sharp focus. Curve length measurement (R) is determined by measuring the length of the same lash hair from the root to the tip in small steps. If the lash hair is not clearly distinguishable from the rest of the bundle, the center of the bundle is traced.

As noted above, the cosmetic compositions formulated with the current film-forming pH dependent polymers exhibit persistent tightening and/or curling effects even when subjected to environmental stresses such as increased temperature and humidity. It is contemplated that these substantially resistant compositions of the current invention may maintain the same or similar (within about 10%) tightening and/or curling effects as when initially applied when subjected to temperatures greater than about 72° F., greater than about 75° F., and greater than 80° F. and/or at relative humidities of greater than about 75%, greater than about 80%, and greater than about 85%. It is contemplated that the compounds will maintain its substantial resistance to environmental stresses for periods greater than 3 hours, greater than about 6 hours and greater than about 9 hours.

The following examples further illustrate various specific embodiments of the present invention, without limiting the broad scope thereof.

EXAMPLES

Example 1

Tightening Effect
A. High Heat and Humidity

Two compositions were prepared: (a) a composition with a film-forming pH-dependent polymer of the current composition: 30% EUDRAGIT L100-55 in water; and (b) a High MW PVP: 30% PVP in water.

Tightening measurements were obtained using the Texture Analyzer TA-TX2 set to the following settings: Test Mode—Compression, Pre-test speed—0.5 mm/sec, Test speed—0.1 mm/sec, Post-test speed—0.5 mm/sec, Target mode —force, Force—60 grams, Trigger type —auto (force), and trigger force—5 grams. Bioskin plates (US Cosmetics Corp, Bioskin plate #15, softness 0.66) were used as a substrate for the testing (one for each solution). Prior to use, the tightness of the untreated Bioskin plates (the blanks) was recorded.

Then each polymer solution (0.5 mL) was pipetted onto its respective Bioskin plate and rubbed uniformly with fingertip until dry. The samples were allowed to dry further for 4 h at room temperature and then retested. The samples were then subjected to 85% RH at 80° F. for three hours and then retested.

Percent tightness was calculated as follows:

(|Distance sample−Distance blank|/Distance blank)×100

Where distance sample=distance probe travels after 60 g of force on Bioskin plate with sample, and distance blank=distance probe travels for Bioskin plate with no sample.

As shown in FIG. 1, Eudragit L100-55 was found to have tightening properties that did not significantly change in the presence of humidity and high temperature (80° F.) (@ 27.5% increase), whereas high MW PVP showed a statistically significant drop in its tightening effect from its initial application (greater than 50% drop).

B. Time

The tightening test detailed above was repeated using the following solutions: (a) 30% EUDRAGIT L100-55 in water, and (b) 30% PVP in water. The same protocol was followed with one additional time point at six days following application. As shown in FIG. 2, EUDRAGIT L100-55 exhibited the same tightening effect as the PVP initially (@ 25% increase) and maintained the same tightening effect over the six day period. The PVP showed a statistically significant drop in its tightening effect over the six day period.

Example 2

Curling Effect

Two mascara compositions adjusted to pH>7.5 were prepared:

| CONTROL FORMULA | | EUDRAGIT FORMULA | |
|---|---|---|---|
| Description | Amount | Description | Amount |
| Water | 47.25 | Water | 53.35 |
| Conditioning agent | 0.2 | Conditioning agent | 0.2 |
| Thickener | 0.4 | Thickener | 0.4 |
| Preservative | 1.15 | Preservative | 1.15 |
| Polyquaternium-10 | 0.2 | Polyquaternium-10 | 0.2 |
| Chelating agents | 0.4 | Chelating agents | 0.4 |
| Triethanolamine | 2.1 | Triethanolamine | 2.1 |
| Colorant | 7 | Colorant | 7 |
| Shellac Wax | 4.4 | Shellac Wax | 4.4 |
| VP/Eicosene Copolymer | 2 | VP/Eicosene Copolymer | 2 |
| Carnauba Wax | 5 | Carnauba Wax | 5 |
| Beeswax | 4.1 | Beeswax | 4.1 |
| Paraffin Wax | 9 | Paraffin Wax | 9 |
| Stearic Acid | 5.5 | Stearic Acid | 5.5 |
| Glyceryl esters | 1.5 | Glyceryl esters | 1.5 |
| Isooctahexacontane | 1.2 | Isooctahexacontane | 1.2 |
| Cyclomethicone | 1.5 | Cyclomethicone | 1.5 |
| | | Eudragit S100 | 1 |

The mascara compositions each were applied to a set of false eyelashes mounted on a holding cylinder for fourteen strokes with a mascara brush. After waiting 10 minutes, 14 more strokes of mascara was added. After at least ten minutes of drying time, an image, such as photographic or digital image, was taken from a side view. Percent (%) Curl=[(R−L)/R]×100%. Length measurement (L) was determined by measuring from the root of a bundle and the tip of a lash in sharp focus. Curve length measurement (R) was determined by measuring the length of the same lash hair from the root to the tip in small steps. If the lash hair was not clearly distinguishable from the rest of the bundle, the center of the bundle was traced.

Figure 3:
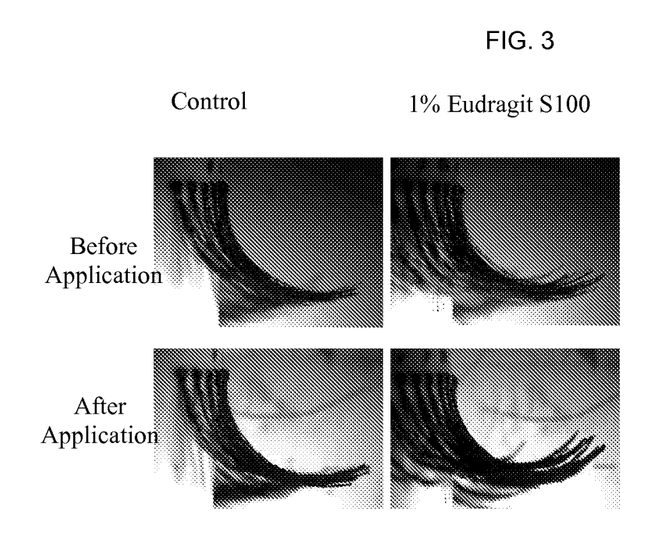
FIG. 3 is a set of four photos illustrating the curling effect upon false eyelashes of a cosmetic composition formulated according to one embodiment of the present invention.

As shown in FIG. 3, the mascara composition with 1% of film-forming pH dependent polymer (EUDRAGIT S100) added increased the curling angle by 5.2° which equaled a 16.7% increase in the curl of the eyelash.

Example 3

Exemplary cosmetic compositions formulated (where applicable) to approximately pH 7.1-8.5 according to the invention are provided in Tables 1 through 6, below.

TABLE 1

| Foundation (Oil-in-Water Emulsion) | |
|---|---|
| Material | Amount (% wt/wt) |
| Waxes | 3-6 |
| Oils | 8-12 |
| Solvent | 25-60 |
| Colorants | 5-15 |
| EUDRAGIT | 0.2-10 |
| Emollients | 8-12 |
| Other Film Former | 2-5 |
| Thickeners | 1-3 |

TABLE 2

Foundation (Water-in-Oil Emulsion)

| Material | Amount (% wt/wt) |
| --- | --- |
| Waxes | 0-5% |
| Oils | 25-50% |
| Solvent | 20-35% |
| Colorants | 5-15% |
| EUDRAGIT | 0.2-10% |
| Emollients | 25-50% |
| Other Film Former | 2-5% |
| Thickeners | 0-1% |

TABLE 3

Mascara

| Material | Amount (% wt/wt) |
| --- | --- |
| Waxes | 15-25% |
| Oils | 0-1% |
| Colorants | 7-10% |
| Solvent | 5-30% |
| EUDRAGIT | 0.2-10% |
| Emollients | 0-1% |
| Other Film Former | 5-25% |
| Thickeners | 1-2% |

TABLE 4

Pressed Powder

| Material | Amount (% wt/wt) |
| --- | --- |
| Waxes | 0.5-2% |
| Oils | 2-15% |
| Colorants | 10-30% |
| EUDRAGIT | 0.2-10% |
| Emollients | 2-15% |
| Other Film Former | 0-2% |

TABLE 5

Liquid Eyeshadow

| Material | Amount (% wt/wt) |
| --- | --- |
| Waxes | 5-15% |
| Oils | 5-20% |
| Colorants | 5-15% |
| Solvent | 10-25% |
| EUDRAGIT | 0.2-10% |
| Emollients | 5-20% |
| Other Film Former | 5-10% |
| Thickeners | 1-3% |

TABLE 6

Aqueous Lip Product

| Material | Amount (% wt/wt) |
| --- | --- |
| Oils | 0-10% |
| Colorants | 3-15% |
| Solvent | 60-90% |
| EUDRAGIT | 0.2-10% |
| Emollients | 0-10% |
| Other Film Former | 0-5% |
| Thickeners | 0.1-3% |

As used in the Examples, "EUDRAGIT" may be EUDRAGIT® S100, EUDRAGIT® L100, and/or EUDRAGIT® L100-55. The inventive cosmetic compositions are expected to have surprising properties, i.e. to provide persistent tightening and/or curling effects on an integument even when subjected to environmental stressors such as increased temperature or humidity. Further as noted within, U.S. patent application Ser. No. 13/325,670 filed Dec. 14, 2011 entitled "Long-Lasting Easy Wash-off Cosmetic Compositions," incorporated herein by reference in its entirety, despite their prolonged effects they may be easily removed by modulation of pH conditions or washing, i.e. by increasing the pH beyond the target pH at which the polymer solubilizes.

The invention having been described by the foregoing description of the preferred embodiments, it will be understood that the skilled artisan may make modifications and variations of these embodiments without departing from the spirit or scope of the invention as set forth in the following claims.

We claim:

1. A method for tightening skin of the neck or face affected by aging, with the proviso that said skin is not the lips, comprising topically applying thereto an effective amount of a pH-dependent film-forming polymer of poly(methacrylic acid-co-methyl methacrylate) with a ratio of methacrylic acid to methyl methacrylate of about 1:1 to about 1:2, an acid value of from about 150 to about 350 mg KOH/g, and a weight average molar mass between about 100,000 and about 150,000 g/mol, in a cosmetically acceptable vehicle to achieve a tightening effect.

2. The method according to claim 1, wherein said ratio of methacrylic acid to methyl methacrylate is about 1:1.

3. The method according to claim 1, wherein said ratio of methacrylic acid to methyl methacrylate is about 1:2.

4. The method according to claim 1, wherein said acid value is from about 150 to about 200 mg KOH/g.

5. The method according to claim 1, wherein said acid value is from about 300 to about 350 mg KOH/g.

6. The method according to claim 1, wherein said pH-dependent film forming polymer has a target pH of greater than about 6.

7. The method according to claim 6, wherein said pH-dependent film forming polymer has a target pH of greater than about 7.

8. A method for tightening skin of the neck or face effected by aging, with the proviso that said skin is not the lips, comprising topically applying thereto an effective amount of a pH-dependent film-forming polymer of poly(methacrylic acid-co-ethyl acrylate) with a ratio of methacrylic acid to ethyl acrylate of about 1:1, an acid value of from about 300 to about 350 mg KOH/g, and a weight average molar mass between about 200,000 and about 350,000 g/mol, in a cosmetically acceptable vehicle to achieve a tightening effect.

9. The method according to claim 8, wherein said pH-dependent film forming polymer has a target pH of greater than about 5.5.

10. The method according to claim 9, wherein said pH-dependent film forming polymer has a target pH of greater than about 6.

11. The method according to claim 10, wherein said pH-dependent film forming polymer has a target pH of greater than about 7.

12. The method according to claim 8, wherein the tightening effect is selected from the group consisting of:
    (a) reduction and/or mitigation of the appearance of fine lines and/or wrinkles;
    (b) improvement in skin tautness;
    (c) improvement in skin appearance negatively impacted by aging and or menopause; and
    (d) reduction or mitigation of the appearance of sagging skin.

13. The method according to claim 8, wherein the tightening effect is an improvement in skin tightness of at least about 10% as compared to skin tightness of skin that has not been treated with said composition.

14. The method according to claim 8, wherein the tightening effect is an improvement in skin tightness of at least about 20% as compared to skin tightness of skin that has not been treated with said composition.

15. The method according to claim 8, wherein the tightening effect is an improvement in skin tightness of at least about 25% as compared to skin tightness of skin that has not been treated with said composition.

16. The method according to claim 8, wherein the pH-dependent film forming polymer is present in an amount of about 0.1 wt % to about 30% of the total weight of the composition.

17. The method according to claim 8, wherein the pH-dependent film forming polymer is not in the form of a microcapsule.

18. A method for providing a curling effect to an eyelash in need thereof comprising applying to said eyelash a cosmetic composition having a cosmetically acceptable vehicle, optionally one or more colorants, and an effective amount of a pH-dependent film-forming polymer of poly(methacrylic acid-co-methyl methacrylate) with a ratio of methacrylic acid to methyl methacrylate of about 1:1 to about 1:2, an acid value of from about 150 to about 350 mg KOH/g, and a weight average molar mass between about 100,000 and about 150,000 g/mol.

19. The method according to claim 18, wherein said ratio of methacrylic acid to methyl methacrylate is about 1:1.

20. The method according to claim 18, wherein said ratio of methacrylic acid to methyl methacrylate is about 1:2.

21. The method according to claim 18, wherein said acid value is from about 150 to about 200 mg KOH/g.

22. The method according to claim 18, wherein said acid value is from about 300 to about 350 mg KOH/g.

23. A method for providing a curling effect to an eyelash in need thereof comprising applying to said eyelash a cosmetic composition having a cosmetically acceptable vehicle, optionally one or more colorants, and an effective amount of a pH-dependent film-forming polymer of poly(methacrylic acid-co-ethyl acrylate) with a ratio of methacrylic acid to ethyl acrylate of about 1:1, an acid value of from about 300 to about 350 mg KOH/g, and a weight average molar mass between about 200,000 and about 350,000 g/mol.

24. The method according to claim 23, wherein said pH-dependent film forming polymer has a target pH of greater than about 5.5.

25. The method according to claim 23, wherein the pH-dependent film forming polymer is present in an amount of about 0.01 wt % to about 20% of the total weight of the composition.

* * * * *